United States Patent [19]

Shaw

[11] Patent Number: 5,158,538
[45] Date of Patent: Oct. 27, 1992

[54] REGULATING PERITONEAL LYMPHATIC DRAINAGE AND USES THEREFOR

[75] Inventor: Howard L. Shaw, Deerfield, Ill.

[73] Assignee: Abbott Laboratories, Abbott Park, Ill.

[21] Appl. No.: 658,448

[22] Filed: Feb. 21, 1991

Related U.S. Application Data

[63] Continuation of Ser. No. 290,962, Dec. 28, 1988, abandoned.

[51] Int. Cl.⁵ .............................................. A61M 1/03
[52] U.S. Cl. ......................................... 604/28; 604/29
[58] Field of Search .................................... 604/27–29; 210/645, 646

[56] References Cited

U.S. PATENT DOCUMENTS

| | | | |
|---|---|---|---|
| 3,989,622 | 11/1976 | Marantz | 210/645 |
| 4,131,544 | 12/1978 | Elahi | 210/670 |
| 4,133,891 | 1/1979 | Nolph | 604/28 |
| 4,339,433 | 7/1982 | Kartinos et al. | 604/29 |
| 4,650,587 | 3/1987 | Polak et al. | 210/638 |
| 4,673,385 | 6/1987 | Popovich et al. | 604/29 |
| 4,756,838 | 7/1988 | Veltman | 210/646 |

FOREIGN PATENT DOCUMENTS

| | | | |
|---|---|---|---|
| 89135 | 9/1983 | European Pat. Off. | 604/29 |
| 2132914 | 7/1984 | United Kingdom | 604/29 |
| 2154469 | 9/1985 | United Kingdom | 604/29 |

OTHER PUBLICATIONS

McGraw-Hill Encyclopedia of Science & Technology, 6th ed. ©1987 pp. 204–205.
Mactier, Robert A. et al., "Pharmacological Reduction of Lymphatic Absorption" *Nephron* 50:229–232 (1988).

*Primary Examiner*—Stephen C. Pellegrino
*Assistant Examiner*—Ralph A. Lewis
*Attorney, Agent, or Firm*—Dressler, Goldsmith, Shore, Sutker & Milnamow, Ltd.

[57] ABSTRACT

A method for blocking lymphatic drainage of the peritoneal cavity of a living mammal by introducing into such cavity particles in the range from about 15 to 150 micron in their shortest cross section which particles are substantially non-toxic and initially substantially water-insoluble. The method can be practiced in combination with peritoneal dialysis or with pharmaceutical agent administration into the peritoneum. Compositions suitable for use in such particle administration are provided.

25 Claims, No Drawings

REGULATING PERITONEAL LYMPHATIC DRAINAGE AND USES THEREFOR

This application is a continuation of application Ser. No. 07/290,962, filed Dec. 28, 1988, now abandoned.

FIELD OF THE INVENTION

This invention relates to methods for limiting the lymphatic drainage of the peritoneal cavity in a living mammal (including man) and includes compositions useful in the practice of such methods.

BACKGROUND OF THE INVENTION

In peritoneal dialysis, access to the peritoneal cavity is conventionally accomplished either by using a disposable rigid catheter, or, if repeated dialysis is anticipated, by use of a flexible silicon rubber catheter equipped with a Dacron (polyethylene terephthalate) velour cuff (to permit the formation of bacteria-tight seals between the catheter and the abdominal wall). With the catheter in place, sterile, pyrogen-free dialysis fluid is introduced in 250 ml to 3000 ml (milliliter) aliquots, allowed to equilibrate (dwell), and is subsequently drained and discarded.

In the case of patients being treated with peritoneal dialysis for renal failure, urea and creatinine are principally cleared from whole blood during dialysis. However, dialysis is also used in removing toxins or poisons or life-threatening excesses of total body water in the absence of renal failure when renal excretion of such substances is inadequate or compromised by prerenal factors.

It has been estimated that substantial amounts of the dialysate in the peritoneal cavity are removed therefrom by lymphatic circulation. The dialysate so removed is known to be drained from the peritoneal cavity through lymphatic micropores or stomata. Not only does this drainage undesirably reduce the ultrafiltration rate of substances, such as urea and creatinine from whole blood, but also this drainage loss leads to unwanted side effects, such as hyperglycemia.

Apart from peritoneal dialysis, this drainage loss reduces the efficiency of pharmaceutical agents placed within the peritoneal cavity. In the case of drugs with a low therapeutic ratio, it was heretofore not possible to administer such through the peritoneal cavity because of lymphatic drainage even though such administration would otherwise be beneficial for treatments of, or within, the peritoneal cavity, such as with certain antibiotics, and the like. It would be desirable in the art of pharmacology to have, for purposes of pharmaceutical agent administration in the peritoneal cavity, a lymphatic blocking substance which slowly releases material into the vascular system from the peritoneal cavity. For example, a drug might be associated with a particle which is adapted to slowly biodegrade and/or bioerode in a regulated or predictable fashion, thereby controllably releasing the drug so that it can accomplish its function, such as treating interstitial infection, and the like.

In an effort to block or retard lymphatic drainage from the peritoneal cavity, various drugs have heretofore been tried, such as neostigmine, for example. Such trials have been, so far as now known, impractical or ineffective. In the case of neostigmine, undesirable systemic absorption and unwanted side effects have been observed. So far as now known, no previous means was heretofore known by which lymphatic drainage from the peritoneum could be blocked or reduced without evident undesirable side effects.

Peritoneal lymphatic blockade is believed to be desirable principally for purposes of increasing the dwell-time of substances in the peritoneal cavity which are normally cleared by this system. Such a blockade would presumably improve the quality and efficiency of peritoneal dialysis. Apart from dialysis, it is believed to be possible and desirable to administer pharmaceutical agents through the peritoneal cavity in combination with a suitable blocking agent, or to implant in the peritoneal cavity a biologically active body, such as a synthetic organ (e.g., a pancreas), or the like, in combination with a suitable lymphatic blocking agent, in order to prolong the desired duration of pharmacological action within the mammalian body.

The art needs a new and effective technique and associated means for accomplishing lymphatic blockade of the peritoneum via the peritoneal cavity.

SUMMARY OF THE INVENTION

In a principle aspect, this invention pertains to a method for at least partially blocking the lymphatic drainage of the peritoneal cavity of a living mammal by introducing into such cavity suitably sized preferably substantially non-toxic, substantially water-insoluble particles, but not limited to such particles. In general, such particles have an average size in the range of about 15 to 150 microns.

In another principle aspect, this invention concerns the carrying out of peritoneal dialysis in combination with the presence in the peritoneal cavity of such particles, thereby to reduce and even block the removal of dialysate within the peritoneal cavity by lymphatic circulation.

In another aspect, this invention concerns the concurrent administration of a pharmaceutical agent through the peritoneal cavity of a living mammal, with such particles being present to reduce or even block the drainage of the pharmaceutical agent from the peritoneal cavity via lymphatic circulation. By this aspect one can, if desired, concurrently, while lymphatic blocking is being achieved as taught by this invention, treat a mammal with a pharmaceutical agent which is not otherwise suitable for peritoneal administration or lymphatic administration. For example, such pharmaceutical agent could be toxic if administered systemically. Also, by this aspect one can, if desired, with suitable formulating, achieve a controlled release and take up of a pharmaceutical agent over a predetermined time interval concurrently with lymphatic blocking.

In another aspect, this invention concerns a class of compositions of such particles which are suitable for use in the practice of the foregoing methods.

In another aspect, this invention concerns techniques for removing such particles, particularly biodegradable particles which are initially substantially water insoluble.

In another aspect, this invention concerns the utilization of particles in the techniques provided that are slowly and controllably biodegradable after introduction into a peritoneal cavity.

A principle object of this invention is to provide a new and useful technique for achieving blockage (including regulation of blockage) of lymphatic drainage from the peritoneal cavity in a living mammal. Optionally, this technique may also be practiced in association with another medical treatment of the peritoneum, such as peritoneal dialysis, peritoneal administration of a pharmaceutical agent, or the like.

Another object is to provide techniques for controlling the extent and also the duration of such blockage in a given mammal.

Another object is to provide procedures for using such peritoneal lymphatic blocking techniques in association with other medical treatments, such as those involving peritoneal dialysis and/or pharmaceutical agent administration.

Another object is to provide a new class of physiologically compatible aqueous compositions adapted for the administration and useage of the peritoneal lymphatic blocking agents provided by the present invention.

Other and further aspects, objects, aims, features, purposes, advantages, and the like will be apparent to those skilled in the art from the teachings of the present specification taken with the drawings and appended claims.

DETAILED DESCRIPTION

Particles

In general, any substantially non-toxic, initially substantially water-insoluble type of particle individually having an average size in the range from about 15 to 150 microns can be used in the practice of this invention. A present preference is to employ particles having an average particle size of about 35 to 55 microns in their shortest cross-section.

Preferably, the particles employed are water dispersable for ease in administration and use in the peritoneal cavity. However, water dispersability can be promoted or augmented readily by compounding the particles with an anti-aggregation agent, such as a non-toxic water-soluble, preferably metabolizable surfactant, (i.e., dispersing agent), such as a polyalkoxylated sorbitan ester of a fatty acid, dimethylacetamide, dioctyl sodium sulfosuccinate, egg yolk, phospholipid, ethyllactate, lecithin, polyethylene glycol, polyethylene glycol/Castor oil reaction product, or the like.

As used herein, the term "non-toxic" means that particles used in the practice of this invention, as well as portions thereof, including degraded materials, or by-products derived therefrom, or the like, do not adversely affect, or cause damage to, a patient's life process, or any of its subcritical aspects, including the patient's living tissue, impairment of the central nervous system, severe illness, death, or the like. In this connection, the term "used" has primary reference to the dose or quantity of given particles which are used with a given patient at any given time. Thus, the $LD_{50}$ (lethal dose, 50%), and also the $LC_{50}$ (lethal concentration, 50%), based on intraperitoneal administration of a given group of particles is preferably at least about 10 times the actual dose used.

While particles which remain substantially water insoluble and/or substantially non-biodegradable for extended periods of time can be used in the practice of this invention, so that such particles remain substantially unchanged when in the peritoneal cavity or in the lymphatic ducts for such extended period of time (for example, for at least about one week), it is now preferred to employ in the practice of this invention particles which, though initially substantially water insoluble (as this term is hereinafter defined), have the capacity to biodegrade (as this term is hereinafter defined).

As used herein, the term "water insoluble" means that the starting particles do not substantially dissolve or degrade into water soluble or water dispersable compounds.

Preferably, the particles, after introduction into the peritoneal cavity, remain substantially water insoluble for a predetermined or selected time interval in order to permit the particles to exert a desired peritoneal lymphatic stomata blocking action for a desired time interval after introduction into the peritoneal cavity. It is presently preferred to employ particles which remain substantially insoluble for at least about one hour after being dispersed in aqueous fluid of the type normally found in the peritoneal cavity or in lymphatic ducts. However, particles having longer and/or shorter times of being substantially water insoluble can be used without departing from the spirit and scope of this invention. For example, particles which remain substantially water insoluble for an indefinite period of time after being dispersed in water and introduced into a mammalian peritoneal cavity can be used, if desired, particularly when such particles are biodegradable.

As used herein, the term "biodegradable," or "biodegrade," or other equivalent word forms, means the capacity of a particle, or group of particles, to undergo size reduction, particularly in the physiological environment of the peritoneal cavity and/or lymphatic ducts independently of the exact scientific cause or causes of such size reduction. However, as those skilled in the art will appreciate, factors which can influence particle size reduction under in vivo conditions can include one or more of dissolution, degradation, erosion (including bioerosion), chemical reaction (including hydrogen ion concentration in the vicinity of a particle or particles), microorganism (including bacteria) activity, enzymatic activity, and the like.

The rate of biodegradability for any given biodegradable particle, or group of particles, in such an environment is determined by such factors as just indicated. Preferably, the rate of biodegradability for any group of particles is known before such group is actually employed in the practice of this invention. Preferably, the rate of biodegradability desired in any given situation involving the practice of this invention is pre-selected, and the particular group of biodegradable particles employed in such situation is selected and/or prepared so as to have approximately such pre-selected rate of biodegradability. Examples of suitable biodegradable particles include polysaccharides, such as alginate, chitin, carrageenan, agarose, natural gums, and the like; cellulose and cellulose derivatives, such as methyl cellulose, carboxymethyl cellulose, and the like; fibrous proteins such as collagen, gelatin, elastin, and the like; dextran, lactin, polypeptides, poly amino acids, polyesters, such as polylactides, polyglycolide, poly(caprolactone), poly(caprolactone-co- -valerolactone), and the like; and polyamides, polyanhydrides, poly(ortho esters), polyacrylates, poly(cyano acrylates), poly vinyl pyrrolidone, and phospholipides.

Particles which, for example, slowly become partially or fully dissolved either in the peritoneal cavity or in the lymphatic ducts over a period of time can be used and may be preferred, as when it is desired to block lymphatic stomata in the peritoneal region or cavity only for a predetermined period of time which is approximately coextensive with the period of time desired for a medical treatment which is concurrently being undergone by a human patient, such as during peritoneal dialysis, or during treatment of the peritoneal cavity walls with a pharmaceutical agent, such as an antibiotic being used to combat infection and prevent peritonitis, or the like. After the treatment period, when the particles may serve no further utility, they may be removed without a drainage procedure through dissolution in aqueous body fluids.

Particles which are considered to be substantially biodegradable can be advantageously and preferably employed, particularly when there is no need to continue peritoneal lymphatic blockage after a treatment period. Such biodegradation can occur by various mechanisms. For example, the particles can appear to undergo dissolution or degradation in the environment of the peritoneal cavity or of the lymphatic ducts, or the particles can be enzymatically reduced and converted into metabolizable substances.

Particles which are considered to be substantially nonbiodegradable can be employed when, for example, semipermanent blocking of peritoneal lymphatic ducts is contemplated, as when a treatment is contemplated for the prevention of lymphatic spread of peritoneal tumors, irrespective of whether they are primary or metastatic.

Alternatively, particles which are organic solvent soluble where the solvent is substantially non-toxic can be employed.

Particles which are preliminarily coated with a layer of a substance which, after peritoneal particle administration, controllably degrades or dissolves in a peritoneal or lymphatic tissue environment, can be advantageously used in the practice of this invention. For example, such a coating can be employed when it is desired to enhance water dispersability of a given particle type. Suitable coating materials include, for example, albumin, alginates, gelatin with surfactant properties, gum, acacia, and the like.

In general, for purposes of this invention, coating techniques can be employed which are known in the art, such as, for example, dipping, spray drying, spray coating, and the like.

Particles can also be coated with a biologically active or pharmaceutically active agent. For example, a monoclonal antibody can be coated on the particles for the purpose of binding the antibody to a suitable antigen to prevent the spread of cancer cells, or the spread of infectious or inflammatory processes. Enzymes and/or peptides can also be associated with the particles to achieve regulated drug delivery to the body through lymphatic circulation. Other examples of releasable particle coating agents include antibiotics, hormones, tPa (tissue plasminogen activator), anti-inflammatory agents, and the like.

Any convenient particle preparation method can be used to provide starting particles for use in this invention as characterized herein. Regardless of the method of preparation, before use in the practice of this invention, particles are preferably sized. Any convenient size selection technique can be employed. For example the randomly sized starting particles can be filtered through 30 to 70 micron filters, and the resulting particle size can be subsequently confirmed by a laser scattering technique or particle sizer. U.S. Standard sieves can be employed.

Particles which initially have one average small dimension and which swell in an aqueous environment to another larger dimension can be advantageously used in the practice of the present invention. For example, if such swellable particles are effectively implanted in the peritoneal lymphatic ducts prior to their expansion, and then are allowed to expand in such ducts, increased lymphatic blocking action can presumably be achieved. For instance, particles can be employed which have an initial maximum particle size below about 10 microns, but which, after the passage of a predetermined time interval, swell to an average maximum particle size above about 30 microns. As shown in Table I below, gelatin is an example of such a particle.

Particles which are aspherically shaped or configured so as to have a main body portion and an integrally associated tail portion can be, advantageously used in the practice of the present invention. For example, these particles are believed to offer improved blocking action particularly when lodged in the lip or mouth regions of peritoneal lymphatic ducts compared to the blocking action achievable with, for example, generally spherically shaped particles or the like. For instance, the body of such a particle can range up to about 30 microns in size while the thickness of the tail portion can taper off with the tail being less than about 30 microns in length. As shown in Table I below, an example of such a tapered particle comprises an irregularly shaped albumin or gelatin particle. Both such particles can be prepared as a coarse admixture with a proper particle size being obtained by sieving. Alternatively, polymers in a particulate crystalline form can be sized by sieving.

In general, the particles suitable for use in the practice of this invention can be known materials, as can methods for their preparation, which in itself is advantageous. Examples of suitable biodegradable particles, together with methods for their preparation and sizing, and a brief indication of their performance characteristics in the context of this invention, are provided in Table I below.

TABLE I

| Materials | Particles Method For Particle Making |
|---|---|
| Fibrous Proteins | denaturation, gelation |
| gelatin | coacervation |
| elastin | |
| collegen | |
| polysaccharides | gelation |
| alginates | |
| chitin | |
| carrageenans | |
| agarose | |
| natural gums | |
| cellulose | |
| and derivatives | |
| plasma protein | |
| albumin | denaturation |
| dextran | crosslinking |
| lactin | crosslinking |
| polypeptides | denaturation |
| poly amino acids | crosslinking |
| polyesters | solvent evaporation |
| polylactides | |
| polyglycolide | |
| poly(caprolactone) | |
| poly(lactile/glycolide) | |
| polyamides | gelation |
| polyanhydrides | solvent evaporation |
| poly(ortho esters) | solvent evaporation |
| polyacrylates | gelation |
| poly(cyano acrylates) | gelation |
| poly vinyl pyrrolidone | crosslinking |
| phospholipids | commercially available |

Examples of presently preferred particles for use in the practice of this invention include those comprised of albumin, gelatin, collagen, polylactide, polylactide/polyglycolide, or mixtures thereof. Any one of such materials apparently can be formulated with, or coated with, for example, a pharmaceutical agent, if desired. In general, it now appears that many different materials can be used in forming particles useful in the practice of this invention; however, as those skilled in the art of pharmaceutical agents will readily appreciate, individual pharmaceutical agents may sometimes be inappropriate for incorporation with (including coating) a specific material.

As indicated in Table I (above), duration of particle blocking action can be based, if desired, on the estimated half-life of the particular particles being used in the mammalian peritoneal cavity, or on the estimated half-life of the blocking action desired.

The particle half-life is conveniently measured by in vitro dissolution data or by biodistribution experimentation in an animal (as by placing radio-labeled particles into the peritoneal cavity and tracing their fate).

Particle half-life is determined by many variables, such as molecular weight, manufacturing process, chemical structure, physical properties, biodegradability, dissolution behavior, particle size characteristics, size of the lymphatic vessels, presence of interstitial edema, cirrhosis, esophogeal varices, surgical obliteration of the lymphatics, irradiation, and the like.

In vitro half-life particle determinations are easier to accomplish than in vivo determinations. Because of the nature of the half-life measurement problem, it now appears that it is not possible to provide exact particle half-life information for individual particle types which is applicable generally to all mammals.

Compositions

In general, the particles used in the practice of this invention are preliminarly dispersed in a physiologically acceptable aqueous medium which medium is then used for administration or introduction of particles into the mammalian peritoneal cavity. While any convenient physiologically acceptable aqueous medium can be employed, it is presently preferred to employ a unit dose composition which is generally characterizable as comprising water which has dispersed therein from about $10^2$ to $10^{11}$ particles. The volume of a unit dose is variable, depending upon such factors as the size of the human or animal being treated, and like factors, but typically and conveniently the volume is in the 250 ml to 3000 ml range, though smaller and larger fluid volumes can be used if desired. The aqueous medium used as the vehicle for particle administration preferably has dissolved therein conventional agents which are employed in the art of pharmacology for physiological compatability purposes.

For example, an aqueous precurser composition comprised of only ionic solutes can be, if desired, preliminarily prepared as an intermediate from suitable starting salts (with osmotically active material optionally being present) with the selected particle type or types dispersed therein. In particular, conventional dialysis fluids can serve as suitable precurser compositions in which particles can be dispersed for particle administration.

For example, an aqueous solution for use as such a precurser composition can comprise water which has dissolved therein the following components in the respective amounts indicated in Table 2 below.

TABLE 2

| Physiologically Acceptable Aqueous Media Within Which Particles Can Be dispersed | |
|---|---|
| Component | Quantity Range (millimoles per liter) |
| Total cations (mEq) | about 120–170 |
| (1) sodium$^+$ | about 120–170 |
| (2) potassium$^+$ | about 0–40 |
| (3) calcium$^{2+}$ | about 0–10 |
| (4) magnesium$^{2+}$ | about 0–10 |
| Total anions (mEq) | about 120–170 |
| (5) chloride$^-$ | about 84–125 |
| (6) bicarbonate$^-$ | about 0–80 |
| (7) metabolizable carboxylate$^-$ | about 0–80 |
| (8) Sum (6 + 7) | about 25–80 |
| Total nonionics | about 0–525 |
| (1) carbon dioxide | about 0–25 |
| (2) osmotically active metal | about 0–500 |
| Milliosmolarity | about 260–765 |
| pH | about 5–9 |

Examples of metabolizable carboxylate anions include 1-lactate, pyruvate, d-betahydroxybutyrate, acetoacetate, acetate, and the like.

Examples of nonionic osmotically active materials (which also are preferably metabolizable) include glucose, glycerol, fructose, sorbitol, and the like. Glucose is presently most preferred.

In such a solution the charges of all cations equal the charges of all anions.

Particularly, when human adminstration of such a solution is contemplated, it is preferred that the milliequivalent rate of sodium to chloride therein approximately correspond to the milliequivalent rates of sodium and chloride in normal mammalian blood which ranges from about 1.24:1 to 1.47:1. In the case of a normal human adult, this range is beieved to extend from about 1.24:1 to 1.45:1 and preferably from about 1.33:1 to 1.42:1 and most preferably from about 1.36:1 to 1.42:1. In the case of dialysis fluids, to create an alkalotic condition in a cell or to correct acidosis, the Na:Cl ratio can range as high as to 1.55.

The total quantity, or sum (sigma) of bicarbonate anions and carbon dioxide present in such a solution preferably ranges from 0 to about 55 millimoles per liter of solution.

Such aqueous solutions are known in the art as are methods for their preparation.

Suitable peritoneal dialysis solutions with which particles can be admixed for the practice of this invention are commercially available.

If a non-toxic surfactant is to be used for purposes of particle dispersing or dispersion stabilization, such can be introduced as desired into a composition being prepared for administration.

If desired, a concentrated preliminary dispersion of particles in water can be prepared which is then conveniently merely blended with a preliminarily prepared solute solution, such as a peritoneal dialysis solution. Additional water can, if desired, be added to achieve a desired concentration for actual administration. Blending can take place before administration or in the peritoneal cavity itself.

In one preferred class of such compositions, a fluid containing dispersed or dispersable particles is provided which is suitable for use in the practice of peritoneal dialysis, as indicated above.

In another preferred class of administratable compositions, a pharmaceutical agent is present in the aqueous medium in combination with dispersed particles, each being present in respective amounts sufficient to be pharmaceutically effective. The exact amount of any pharmaceutical agent in a given unit dose can vary greatly, and so no exact quantity ranges can be provided which are individually suitable for all possible pharmaceutical agents and compositions. For example, in the case of antibiotics, a unit dose can contain 0.5 weight percent erythromycin or 4 weight percent bacitracin sulfate along with dispersed particles as described above.

Administration Generally

To achieve blocking of peritoneal lymphatic passages in accord with this invention, one introduces into the peritoneal cavity a quantity of the herein described particles as above indicated. Administration, for example, can be generally accomplished through a catheter, such as one of the type conventionally employed for peritoneal dialysis which constitutes a presently preferred administration technique. Any convenient administration technique can be employed.

In one presently preferred method of administration, the particles are first dispersed in an aqueous medium, and the resulting medium is then introduced into a peritoneal cavity. Presently preferred aqueous dispersions for use in the practice of this invention are dialysis compositions.

In another method of administration, a relatively concentrated, relatively small volume, aqueous dispersion of such particles is first instilled into the peritoneal cavity through a peritoneal catheter or the like, and thereafter a desired dose of dialysis fluid is administered through the catheter and admixed internally within the peritoneal cavity with such particle dispersion.

The quantity of particles administered in a unit dose is usually at least sufficient to achieve a partial blocking of peritoneal lymphatic stomata.

As those skilled in the art will readily appreciate, the number of particles administered in a single dose is influenced by the extent of peritoneal lymphatic blocking desired or intended. In turn, the extent of blocking achieved is related to the estimated surface area of the peritoneal cavity being treated, and to the estimated number of lymphatic stomata per unit of such surface area. For example, when maximal lymphatic blockage is desired in the peritoneum, the number of particles introduced to the peritoneal cavity is preferably at least about equal to the estimated number of lymphatic stomata present in the treated mammal's peritoneal cavity. An estimate of this number is readily determinable for a given mammal.

For example, it has previously been reported that the rat has about $10^4$ lymphatic stomata per square centimeter of peritoneal surface area with a total diaphragmatic peritoneal surface area of about 15 square centimeters. An adult human has about $10^4$ lymphatic stomata per square centimeter of peritoneal surface area with a total diaphragmatic peritoneal surface area of about 1000 square centimeters. Variations in density of lymphatic stomata per square centimeter of peritoneal surface area, and variations in total diaphragmatic peritoneal surface area occur from infancy to adulthood in apparently all mammalian species, including man. The majority of lymphatic stomata available in the region of the peritoneal sac for peritoneal absorption are in the diaphragm. Hence, wide variations in the number of particles administered as part of a dose rate occur when such variables as the age and condition of a given patient are taken onto account.

A present preference is to limit the total number of particles introduced in a single dose into a given mammal's (including a man's) peritoneal cavity to a value which is not more than about 10 times the maximum estimated number of lymphatic stomata present therein. A larger number of particles, if desired, can be employed without departing from the spirit and scope of the invention.

The introduction of a substantially larger total number of particles than a value based upon a so-calculated and estimated number of total lymphatic stomata in the peritoneal cavity may be desirable for inclusion in a single dose to aid in distributing particles throughout a peritoneal cavity and over the surface portions of such cavity, thereby to increase and maximize peritoneal lymphatic blockage.

Those skilled in the art will readily appreciate that a particular particle count for a given particle unit dose can be larger or smaller than these indicated illustrative values, depending upon many variables, and no limitation upon the present invention is to be inferred from these illustrative values.

A term such as "single dose," or "unit dose," as used herein does not mean that administration necessarily involves the introduction of the entire dose at a given time. It may be that, because of half-life considerations measured against the duration of blocking action desired, that a "single dose" or "unit dose" will occur over a definite period of time, such as 4 to 8 hours.

To maintain a high or even maximal level of peritoneal lymphatic blockage in a mammal, it may be desirable to use a "booster" or supplemental particle dose into a given peritoneal cavity, particularly in order to compensate for the rate of particle deterioration, as from dissolution, biodegradation, or the like. The quantity of particles to be present in such a supplemental dose can be estimated based upon the variables involved in any particular situation. For example, in the case of particles composed of gelatin, the particle deterioration rate, or the particle half-life, can be selectively determined, so that the number of particles to be administered in a supplemental dose can be estimated so as to maximize the peritoneal blockage effect in a human adult peritoneal cavity over a prolonged period of blockage maintenance.

As indicated above, commonly, the administration of particles to accomplish lymphatic blocking in the peritoneal cavity takes place in combination with at least one other medical treatment, such as a treatment involving peritoneal dialysis, a treatment involving pharmaceutical agent (drug) therapy, or the like. For such purposes, the particles used are introduced into the mammalian peritoneal cavity either immediately preceding, or concurrently during, introduction of the agents used for such other medical treatment(s), such as a peritoneal dialysis fluid, or a drug. Whether administered before, concurrently with, or during treatment after administration of such other agents being used for medical treatment, the particles are employed at dose rates such as are hereinabove indicated.

For example, the invention can be utilized to enhance an acute dialysis requiring several hours to a more extended period of about one month.

When the particles themselves have been prepared (or treated) so as to incorporate a pharmaceutical agent which is to be released over a predetermined half-life, the invention can be utilized to enhance or extend the duration of drug administration at a desired dose release rate; the exact duration and release rate depending upon the clinical indication and other factors. In connection with a therapeutic effect, the particles by themselves can be administered for the prevention of, for example, metastasis of a tumor spreading via peritoneal lymphatocs or elsewhere in the body.

Also, if desired, the particles by themselves can be administered for the prevention of spread of infection by the same mechanism.

Administration for Peritoneal Dialysis

The technique for conducting peritoneal dialysis in accordance with the present invention involves the steps of (A) introducing into the peritoneal cavity of a living mammal (including especially man) particles as hereinabove described, (B) introducing into said peritoneal cavity a peritoneal dialysis fluid, (C) retaining the resulting mixture of said fluid and said dispersion in said peritoneal cavity for a time period which is at least sufficient to achieve urea removal from said mammal through said mammal's peritoneum and into said resulting mixture in said peritoneal cavity, and (D) removing said resulting mixture from said peritoneal cavity.

As regards the "introducing" steps (above), step (A) can precede step (B), and/or both steps (A) and (B) can be practiced concurrently. In the last situation, the particles can be dispersed, if desired, in the dialysis fluid prior to the time when the dialysis fluid is introduced into the peritoneal cavity, or the dialysis fluid can be mixed with an aqueous dispersion of particles at the time when both such fluid and such dispersion are being introduced into a peritoneal cavity. Regardless of step sequence, the introducing can be accomplished by the techniques used in conventional peritoneal dialysis.

In general, the quantity of such particles so introduced is at least sufficient to reduce the rate of removal of such resulting mixture from the treated mammal's peritoneal cavity through the mammal's lymphatic stomata during the retention period of the resulting mixture in such peritoneal cavity compared to the quantity of dialysis fluid so removed in such peritoneal cavity when no such particles are present. A presently preferred dose rate is in the case of a human adult is in the range of from about $10^2$ to $10^9$ total particles per each peritoneal dialysis procedure, though more or less particles can be employed without departing from the spirit and scope of the invention. In general, the total number of particles so introduced is at least equal to the estimated number of lymphatic stomata in the treated peritoneal cavity. Particle size is as above indicated, as is particle composition.

As those skilled in the art will readily appreciate, if and when the particles themselves contain, or are associated with glucose, the glucose will contribute to the dialysis. Similarly, if and when the particles themselves are osmotically active or biodegrade or dissolve to produce osmotic agents, such agents will also contribute to dialysis. Also, if and when the particles themselves contain, or are associated with, amino acids, peptides, or proteins, such can contribute to the nutritional status of the patient. Further, if and when the particles themselves contain, or are associated with, the so-called ketoacids, such ketoacids will reduce the urea load on the patient and may also further aid in the dialysis process.

As regards steps (C) and (D) above, the residence time of a mixture containing particles in the peritoneal cavity, and also the procedure for mixture removal from the peritoneal cavity, are similar to the retention time and removal procedures heretofore conventionally employed in peritoneal dialysis. No special procedures or precautions need be followed when utilizing the particles.

Step (D) ("removing") is carried out either by using biodegradable particles, or by flushing the peritoneal cavity. After a flushing operation is completed, however, fluid and particles will be retained in the peritoneal cavity. The fluid remaining is subsequently gradually removed from the peritoneal cavity by ultrafiltration, while the particles remaining are removed by biodegrading (as this term is defined herein).

Drug Administration

To employ particle administration with pharmaceutical agent administration into the peritoneal cavity of a living mammal (including especially a human being), one follows the procedural steps of (A) introducing into the peritoneal cavity of such mammal an aqueous dispersion of particles as hereinabove characterized, and (B) introducing into said peritoneal cavity a pharmaceutical agent in an amount at least sufficient to provide a pharmaceutically effective dose of such agent for such mammal.

The pharmaceutical agent is either in a form which is absorbable through said mammal's peritoneum, or is in a controlled release form whereby the agent is released into the peritoneal cavity over a predetermined time period.

The resulting mixture of an aqueous dispersion and a pharmaceutical agent is retained in the peritoneal cavity for a time which is at least sufficient to effect at least a partial absorption or adsorption of the pharmaceutical agent through the mammal's peritoneum. Thereafter, the resulting mixture can either be removed from the peritoneal cavity by drainage, as through a catheter or the like, or naturally through peritoneal lymphatic micropores (stomata) drainage. In the latter situation, the particles are preliminary chosen either to be biodegradable (including dissolved), over a period of time generally coextensive with the period of treatment contemplated for the pharmaceutical agent, or bioerodable.

In this administration procedure, step (A) can precede step (B), step (B) can precede step (A), and/or steps (B) and (A) can be practiced concurrently. If the last indicated procedure is followed, then the aqueous particle dispersion and the pharmaceutical agent can either be combined together into a mixture prior to the introducing, or the pharmaceutical agent and the dispersion can be combined together during or even immediately after the introducing. The pharmaceutical agent can be coated upon, distributed within, or otherwise physically or even chemically associated with a class of particles prior to administration.

Preferably, the quantity of particles introduced into the peritoneal cavity is at least sufficient to reduce the rate of removal of pharmaceutical agent from the peritoneal cavity through the peritoneal lymphatic stomata compared to the rate of removal of the pharmaceutical agent from the peritoneal cavity through the peritoneal lymphatic stomata therein when particles are not present in such peritoneal cavity. Since this result appears to be achieved when the total number of particles so introduced is at least equal to the estimated number of lymphatic stomata in the peritoneal cavity, it is presently preferred to introduce at least this particle quantity during the administration of the pharmaceutical agent.

Selection of, and preferences for, particle size and structure can be as above indicated herein with particle preferences being generally as described above.

Any desired pharmaceutical agent can be utilized in the practice of the present invention. Present examples include antibiotics, nutrients, hormones, peptides, proteins, artificial pancreas systems, analgesics, diuretics, vasodilators, and the like.

Also, various biologically active agents can be utilized in the practice of the present invention. For example, oncolytic monoclonal antibodies, which are coated upon or infused into particles before administration for controlled release during lymphotic blocking, can be used.

One suitable release system comprises a matrix system or a layered sequence of pharmaceutical agent with particle material in a particle structure. When a biodegradable material, for example, albumin, is used as the particle material, and a particle employs alternate layers of particle material and pharmaceutical agent, the pharmaceutical agent is gradually released at a controlled rate.

Conveniently and preferably, such a pharmaceutical agent is introduced in aqueous solution for ease in administration. However, solution forms may not always be possible or convenient. When such is the case, the administration is carried out by compounding the pharmaceutical agent with means adapted to regulate the rate of release of the pharmaceutical agent into the peritoneal cavity. The rate of release is, of course, selected so as to be compatible with the time period intended for the peritoneal lymphatic action achieved by the practice of the present invention.

As those skilled in the art will appreciate, if at the time of flushing, the particles have passed into the lymphatic circulatous system, they cannot be removed by flushing. In such event, the particles can only be removed by biodegradation or dissolution, although the flow of further instilled fluids may promote particle removal or biodegradation.

Particle Removal

Particle removal from the peritoneal cavity can be divided into phases. In a first phase, residual liquid containing dispersed particles is drained from the peritoneal cavity. In subsequent phases, further removal of particles is accomplished.

In general, biodegradable particles can be removed by in vivo action so that no particle separation procedure needs to be employed. As indicated above, non-deteriorating (e.g., non-biodegradable and non-dissolving) particles may desirably be removed from the peritoneal cavity, or, more specifically, from the openings or micropassages of lymphatic ducts in the peritoneum, at some desired time, for example, after a given medical treatment has been accomplished, or otherwise, if desired.

Biodegradation is presently a preferred removal technique, as indicated.

If it is desired to achieve a predetermined particle removal profile or pattern independently of biodegradation, various techniques can be employed. For example, mixtures of different types of particles can be employed in a given dose.

Discussion

It is believed that the particles employed in the practice of this invention produce blockage of lymphatic stomata in the peritoneum for varying durations. Employing, for example, particles of gelatin which hydrolyze and degrade into relatively innocuous materials, results in removal of particles after a predeterminable time interval. The effect is believed to obviate any danger of producing ascites which could possibly result from a permanent blockage of peritoneal lymphatic stomata. Although the larger particles will block the lymphatic lining surrounding the peritoneum, the smaller particles will probably travel further into lymph nodes along the path of lymphatic circulation. Blockage of these lymph nodes near their starting stomata may enhance the total lymphatic blockade.

By blocking lymphatic drainage of the peritoneal cavity, the effectiveness of the ultrafiltration produced by peritoneal dialysis is increased, which increases the efficiency of peritoneal dialysis. Thus, over a given period of time, the effectiveness of peritoneal dialysis is increased while the requisite volume of dialysate used to achieve the resulting effect is reduced.

It now appears that blood sugar levels can be lowered during peritoneal dialysis, and urea clearance can be increased by up to about 20%, with the same number of exchanges per day. Fewer exchanges probably are necessary to achieve the same urea clearance. As those skilled in the art will appreciate, when blood sugar levels are kept down, such as is achievable by the practice of the present invention, then hyperinsulinemia is reduced, and, as a consequence, there is a lessened incidence of hyperlipidemia.

In the case of pharmaceutical agents, the blocking of lymphatic drainage of the peritoneal cavity by the practice of this invention permits achievement of prolonged drug action or of prolonged action of other therapeutic or diagnostic agents whose mode of action is either in the peritoneum or elsewhere in the mammalian body. For example, in the case of those antibiotics, such as Bacitracin or the like, that are currently considered toxic if administered systemically, it may be possible to administer such into the peritoneal cavity, particularly if lymphatic blocking is substantially complete. The present invention permits a higher local concentration of pharmaceutical agent to be achieved than heretofore attainable without the detrimental systemic effects. Ordinarily, antibiotics are given systematically to produce local effects. This invention reverses this process.

If, for example, selected alginate particles hydrolyze slowly, then a pharmaceutical unit dose can involve a 100 milliliter aqueous dispersion containing a mixture of such particles which are introduced to the peritoneal cavity for retention times ranging from about a day up to about 30 days.

Embodiments

The following examples are offered to specifically illustrate the invention and are not to be construed as limiting the scope of the invention.

EXAMPLES 1-4

Dispersion Preparation

Spherical polystyrene (PS) particles in hatch sizes of, respectively, (1) about 10 microns, (2) about 16 microns, (3) about 20 microns, and (4) about 43 microns (obtained commercially from Coulter Labs, Hialeah, Fla.) were washed to remove residual surfactant materials, and then were mixed into a peritoneal protein aqueous formulation having the following composition: human albumin, 4.38 g/dL plus 3 mg/g Evans blue (T-1824 Gurr, London, England).

EXAMPLES 5-7

Dispersion Preparation

Additionally, spherical polymethylmethacrylate (PMMA) particles in batch size ranges of, respectively, (a) about 6 to 32 microns, (b) about 13 to 58 microns, and (c) about 19 to 64 microns (obtained commercially from Polysciences, Inc., Warrington, Pa.) were similarly washed as in Examples 1-4.

The PMMA spheres were each then prepared as a 10 g/dl suspension in physiological saline to which had been added 0.3 g/dl of "Tween" 80, a polyoxyalkylene derivative of a fatty acid partial ester of sorbitol anhydride, a surfactant (obtained commercially from ICI). The resulting dispersion was subjected to ultrasonic mixing for about 5 minutes to help suspend the particles.

EXAMPLE 8

Demonstration

Procedure

Forty male hooded Wistar rats were divided randomly into eight groups of five animals, fed on rat nuts, and maintained at 21° C., and their weights recorded.

Intraperitoneal injections of the polystyrene dispersions of Examples 1-4 and the polymethylmethacrylate dispersions of Examples 5-7 were accomplished according to the dose rates set forth in Table 3 below:

TABLE 3

| | Rat Dosages of Particles | | |
|---|---|---|---|
| Ex. No. | Particle Used | Measured Mean Diam. (Microns) | Size Range (Microns) | Dose/Rat |
| 1. | Polystyrene | 9.79 | 13.0-7.9 | 0.5 ml |
| 2. | Polystyrene | 15.67 | 21.5-13.0 | 0.9 ml |
| 3. | Polystyrene | 20 | 37.6-13.0 | 0.9 ml |
| 4. | Polystyrene | 43 | 53.5-37.6 | 2.5 ml |
| 5. | PMMA (brown) | 6-32 | 188-7.9 | 0.2 ml |
| 6. | PMMA (blue) | 13-58 | 188-16.7 | 1.0 ml |
| 7. | PMMA (red) | 19-64 | 188-13.0 | 3.7 ml |

Four hours later, the animals were anesthetized with intraperitoneal urethane and investigated according to the procedure set out in Casley-Smith (Microcirculation, Endothelium and Lymphatics 2 (1985) 385-415), but with the modifications that only one intraperitoneal pressure (25 mm Hg) and only one test solution (human albumin, 4.38 g/dl, plus 3mg/g of Evan's blue-T1824, Gurr, London) was used.

In brief, the procedure involves wrapping the rat in adhesive bandage from the mid-thorax to the inguinal region (to prevent excessive dilation at the peritoneal cavity, with excessive solution quantities being needed). The animals were given artificial respiration (because anesthesia considerably reduces lymphatic uptake from the peritoneal cavity). During testing, each was in a supine position. The test solution was administered via a multi-holed cannula which was glued in place with a cyanoacrylate ester. The equipment was siliconized.

The test solution was administered under pressure (checked with a strain-gauge) and the total volume which flows in was measured. The experiment was run for times which varied with the rate of inflow. At its conclusion, the cavity was emptied by reducing the pressure to −10 cm water. (Pilot studies have shown that this results in complete emptying with an error of less than 0.5 ml.)

The Evan's blue concentration (and hence that of the administered albumin protein) was estimated using a spectrophotometer (at 615±2 nm) and the total protein was estimated (at 290±2 nm). Thus, alterations in the administered protein concentration were measured (plus any additional protein coming from the body). The alteration can be substantial if concentrations of albumin are used other than 4.38 g/dl). Using equations 4 and 10 of Casley-Smith (loc. cit.), the protein and water uptake via the diaphragmatic initial lymphatics were calculated. Lymphatic fluid uptake is shown in Table 4 below.

TABLE 4

| Lymphatic fluid update (ml/kg/hr) (milliliters per kilogram per hour per rat) | | | | | | | |
|---|---|---|---|---|---|---|---|
| | Run 1 | Run 2 | Run 3 | Run 4 | Run 5 | Mean | Std. Dev. |
| Control | 148.16 | 150.13 | 148.22 | 150.55 | 131.34 | 136.71 | 190.28 |
| Ex. 1 | 159.31 | 139.74 | 127.06 | 136.06 | 114.4 | 135.44 | 16.601 |
| Ex. 2 | 98.611 | 70.633 | 67.819 | 93.345 | 84.407 | 82.96 | 12.866 |
| Ex. 3 | 52.874 | 44.287 | 32.543 | 30.213 | 48.795 | 41.74 | 9.971 |
| Ex. 4 | 14.52 | 13.761 | 6.7964 | 14.944 | 13.276 | 12.54 | 3.304 |
| Ex. 5 | 16.271 | 10.537 | 7.653 | 14.807 | 13.879 | 12.63 | 3.490 |
| Ex. 6 | 36.134 | 25.526 | 27.963 | 45.306 | 39.867 | 34.96 | 8.225 |
| Ex. 7 | 26.821 | 17.009 | 13.223 | 15.887 | 28.51 | 20.29 | 6.898 |

Results and Discussion

As the results show (see FIG. 1 and Table 4), the particles having mean diameters of 45, 40, 55 and 84 microns reduced very considerably the lymphatic uptake of fluid (and protein). The particles with mean diameters in the 40 to 45 micron range reduced lymphatic uptake of fluid to less than 10 percent of the control. Although the 21 micron mean diameter particles were nearly the mean size of the initial lymphatic stomata (about 25 microns), such particles only reduced uptake to about 30% of the control.

Although the present invention has been described and illustrated based on the presently available information and embodiments, it is to be understood that modifications and variations are within the spirit and scope of the invention, as those skilled in the art will readily appreciate and that such are within the purview and scope of the appended claims.

I claim:

1. A method for blocking lymphatic drainage of the peritoneal cavity of a living mammal comprising the step of introducing into said peritoneal cavity an aqueous dispersion of biodegradable, substantially non-toxic, initially substantially water-insoluble particles that slowly become partially or fully dissolved in the peritoneal cavity or in the lymphatic ducts of said mammal, said particles comprised of at least one material selected from the group consisting of polysaccharides, cellulose and cellulose derivatives, fibrous proteins, plasma proteins, dextran, lactin, polypeptides, polyamino acids, polyesters, polyamides, polyanhydrides, poly(ortho ester), polyacrylates, poly(cyano acrylates), polyvinyl pyrrolidone, phospholipids, polystyrene and polymethylmethacrylate, said particles individually having an average size of about 15 to 150 microns in their shortest cross-section wherein the total number of said particles introduced is at least equal to the estimated number of lymphatic stomata in said peritoneal cavity.

2. The method of claim 1 wherein at least some of said particles are coated.

3. The method of claim 1 wherein said dispersion contains from about $10^2$ to $10^{11}$ particles.

4. The method of claim 1 wherein the volume of said dispersion so introduced is from about 250 to 3000 milliliters.

5. The method of claim 1 wherein said particles have a particle size distribution of about 35 to 55 microns.

6. The method of claim 1 wherein said particles as initially introduced have a small average size, but which, after the passage of a predetermined time interval, swell to an average size in the range from about 15 to 150 microns.

7. The method of claim 1 wherein said introduction is carried out either before or during a peritoneal dialysis procedure using said peritoneal cavity.

8. The method of claim 1 wherein said introduction is carried out either before or during administration of a pharmaceutical agent to said peritoneal cavity.

9. An improved method for conducting peritoneal dialysis comprising the steps of:
A. introducing into the peritoneal cavity of a living mammal water dispersable, biodegradable, substantially non-toxic, initially substantially water-insoluble particles that slowly become partially or fully dissolved in the peritoneal cavity or in the lymphatic ducts of said mammal, said particles comprised of at least one material selected from the group consisting of polysaccharides, cellulose and cellulose derivatives, fibrous proteins, plasma proteins, dextran, lactin, polypeptides, polyamino acids, polyesters, polyamides, polyanhydrides, poly(ortho esters), polyacrylates, poly(cyano acrylates), polyvinyl pyrrolidone, phospholipids, polystyrene and polymethylmethacrylate, said particles individually having an average size in the range from about 15 to 150 microns in their shortest cross-section wherein the total number of said particles introduced is at least equal to the estimated number of lymphatic stomata in said peritoneal cavity;
B. introducing into said peritoneal cavity a peritoneal dialysis fluid;
C. retaining the resulting mixture of said fluid and said dispersion in said peritoneal cavity for a time period which is at lest sufficient to achieve urea removal from said mammal through said mammal's peritoneum and into said resulting mixture in said peritoneal cavity; and
D. removing said resulting mixture from said peritoneal cavity.

10. The method of claim 9 wherein step (A) predeces step (B).

11. The method of claim 9 wherein step (A) and step (B) are practiced concurrently.

12. The method of claim 9 wherein said particles are dispersed in said dialysis fluid prior to said introduction.

13. The method of claim 9 wherein the quantity of said particles so introduced is at least sufficient to reduce the rate of removal of said resulting mixture from said peritoneal cavity through said mammal's lymphatic stomata during said retention compared to the quantity of dialysis fluid so removed when no such particles are present.

14. A method for administering a pharmaceutical agent into a living mammal comprising the steps of:
A. introducing into the peritoneal cavity of a living mammal water dispersable, biodegradable, substantially non-toxic, initially substantially water-insoluble particles that slowly become partially or fully dissolved in the peritoneal cavity or in the lymphatic ducts of said mammal, said particles comprised of at least one material selected from the group consisting of polysaccharides, cellulose and cellulose derivatives, fibrous proteins, plasma proteins, dextran, lactin, polypeptides, polyamino acids, polyesters, polyamides, polyanhydrides, poly(ortho esters), polyacrylates, poly(cyano acrylates), polyvinyl pyrrolidone, phospholipids, polystyrene and polymethylmethacrylate, said particles individually having an average size in range from about 15 to 150 microns in their shortest cross section wherein the total number of said particles introduced is at least equal to the estimated number of lymphatic stomata in said peritoneal cavity; and
B. introducing into said peritoneal cavity a pharmaceutical agent in an amount at least sufficient to provide a pharmaceutically effective does of said agent for said mammal; said pharmaceutical agent being in a form which is absorbable by said mammal through said mammal's peritoneum.

15. The method of claim 14 wherein the resulting mixture of said aqueous dispersion and said pharmaceutical agent is retained in said peritoneal cavity for a time at least sufficient to effect at least a partial absorption of said pharmaceutical agent through said mammal's peritoneum.

16. The method of claim 15 wherein after said retaining time said resulting mixture is thereafter removed from said peritoneal cavity.

17. The method of claim 14 wherein step (A) precedes step (B).

18. The method of claim 14 wherein step (A) and step (B) are practiced concurrently.

19. The method of claim 18 wherein said aqueous dispersion and said pharmaceutical agent are combined together into a mixture prior to said introduction.

20. The method of claim 14 wherein the quantity of said particles so-introduced is at least sufficient to reduce the rate of drainage of said pharmaceutical agent from said peritoneal cavity through lymphatic stomata therein compared to the rate of drainage of said pharmaceutical agent from said peritoneal cavity through lymphatic stomata therein when said particles are not present in said peritoneal cavity.

21. The method of claim 18 wherein said pharmaceutical agent as so-introduced is in combination with means regulating the rate of release of said pharmaceutical agent into said peritoneal cavity.

22. A composition adapted for introduction into the peritoneal cavity of a living mammal and which, when so-introduced into such a peritoneal cavity as a unit dose, is adapted to reduced lymphatic drainage from such peritoneal cavity, said composition comprising water which has dispersed therein per unit dose from about $10^2$ to $10^{11}$ particles which are biodegradable, substantially non-toxic, initially substantially water-insoluble, and slowly become partially or fully dissolved in the peritoneal cavity or int he lymphatic ducts of said mammal, said particles comprises of at least one material selected from the group consisting of polysaccharides, cellulose and cellulose drivatives, fibrous proteins, plasma proteins, dextran, lactin, polypeptides, polyamino acids, polyesters, polyamides, polyanhydrides, poly(ortho ester), polyacrylates, poly(cyano acrylates), polyvinyl pyrrolidone, phospholipids, polystyrene and polymethylmethacrylate, and said particles have an average particle size in the range from about 15 to 150 microns in their shortest cross section.

23. A composition of claim 22 which additionally contains a pharmaceutical agent.

24. A composition of claim 23 which is adapted for use as a peritoneal dialysis fluid.

25. The composition of claim 23 additionally containing means for releasing said pharmaceutical agent at a predetermined controlled rate.

* * * * *

UNITED STATES PATENT AND TRADEMARK OFFICE
CERTIFICATE OF CORRECTION

PATENT NO. : 5,158,538             Page 1 of 2
DATED : October 27, 1992
INVENTOR(S) : Shaw It is certified that error appears in the above-identified patent and that said Letters Patent is hereby corrected as shown below:

Column 4, Line 31    The words "in vivo" should be italized.

Column 7, Line 21    The words "in vitro" should be italized.

Column 7, Line 31    The words "In vitro" should be italized.

Column 7, Line 32    The words "in vivo" should be italized.

Column 13, Line 62    The words "in vivo" should be italized.

Column 15, Line 9    Delete the word "hatch" and insert the word --batch--.

Column 19, line 6    Delete the words "int he" and insert the words --in the--.

UNITED STATES PATENT AND TRADEMARK OFFICE
CERTIFICATE OF CORRECTION

PATENT NO. : 5,158,538
DATED : October 27, 1992
INVENTOR(S) : Shaw

It is certified that error appears in the above-indentified patent and that said Letters Patent is hereby corrected as shown below:

Column 19, Line 7, Delete the word "comprises" and insert the word --comprised--.

Signed and Sealed this

Twenty-fifth Day of January, 1994

Attest:

BRUCE LEHMAN

*Attesting Officer*  *Commissioner of Patents and Trademarks*